(12) United States Patent
Lastre González et al.

(10) Patent No.: US 7,648,709 B2
(45) Date of Patent: Jan. 19, 2010

(54) ALLERGY VACCINE COMPOSITION, PRODUCTION METHOD THEREOF AND USE OF SAME IN ALLERGY TREATMENT

(76) Inventors: Miriam de San Juan Bosco Lastre González, Calle 66 No. 913 e/ 9 y 11, Playa, Ciudad de la Habana 11300 (CU); Oliver Germán Pérez Martín, Calle 66 No. 913 e/ 9 y 11, Playa, Ciudad de la Habana 11300 (CU); Alexis Labrada Rosado, Edificio 3 Apto 4 Comunidad Cientifica, Bejucal, La Habana 6048 (CU); Igor Bidot Martínez, San Lino No. 1101 e/ Varona y Pintó, Guantánamo (CU); Gustavo Rafael Bracho Granado, Calle 124 No. 2509 e/ 25 y 27, Rpto Zamora, Marianao, Ciudad de la Habana (CU); Judith Mónica Del Campo Alonso, Calle 23 No. 508 Apto 3B e/ G y H, Plaza de la Revolución, Ciudad de la Habana 10400 (CU); Dainerys Aleida Pérez Lastre, Calle 66 No. 913 e/ 9 y 11, Playa, Ciudad de la Habana 11300 (CU); Elisa Facenda Ramos, Calle 14 No. 41120 e/ 15 y 17, Santiago de Las, Vegas, Boyeros, Ciudad de la Habana (CU); Caridad Zayas Vignier, Calle 27D No. 12212 e/ 122 y 122, Marianao, Ciudad de la Habana (CU); Claudio Rodríguez Martínez, Edificio 2 Apto 4, Comunidad Cientifica, Bejucal, La Habana 6048 (CU); Victoriano Gustavo Sierra González, Calle 158 No. 3114 e/ 31 y 33, Playa, Ciudad de la Habana 16017 (CU); Jorge Ernesto Pérez Lastre, Calle 66 No. 913 e/ 9 y 11, Playa, Ciudad de la Habana 11300 (CU)

( * ) Notice: Subject to any disclaimer, the term of this patent is extended or adjusted under 35 U.S.C. 154(b) by 254 days.

(21) Appl. No.: 10/513,493

(22) PCT Filed: May 8, 2003

(86) PCT No.: PCT/CU03/00007

§ 371 (c)(1),
(2), (4) Date: Jan. 19, 2006

(87) PCT Pub. No.: WO03/094964

PCT Pub. Date: Nov. 20, 2003

(65) Prior Publication Data

US 2006/0110435 A1 May 25, 2006

(30) Foreign Application Priority Data

May 8, 2002 (CU) .......................... 91/02

(51) Int. Cl.
*A61K 39/095* (2006.01)
*A61K 39/35* (2006.01)

(52) U.S. Cl. .............. 424/249.1; 424/275.1; 424/282.1

(58) Field of Classification Search .................. None
See application file for complete search history.

(56) References Cited

FOREIGN PATENT DOCUMENTS

WO  WO02072012  * 9/2002

OTHER PUBLICATIONS

Slater et al., J. Allergy Clin. Immunol., 105:468-474, 2000.*
Ferrandiz et al., Abstract 175, J. Allergy Clin. Immunol., 97:226, 1996.*
Sewer et al., Int. Arch. Allergy Immunol., 123:242-248, 2000.*
Ferrandiz et al., Int. Arch. Allergy Immunol., 116:206-214, 1998.*

* cited by examiner

*Primary Examiner*—Robert B Mondesi
*Assistant Examiner*—Brian J Gangle
(74) *Attorney, Agent, or Firm*—Lackenbach Siegel, LLP

(57) ABSTRACT

The present invention relates to the field of Immunology, specifically with the branch of Immuno-Allergy and in particular with the use of adjuvant or carrier compounds, capable of modulating the immune response to allergens. The technical objective that is pursued is to obtain a pharmaceutical preparation of therapeutic or prophylactic use using bacterial proteoliposomes, which transform the allergic response Th2 and IgE when being applied in allergic individuals, toward a protector response Th1; as well as it is able to prevent the appearance and the development of allergies in individuals non-allergic yet. The vaccine composition consists of proteoliposomes derived from Gram-negative bacteria coupled to allergens and optionally contains other adjuvants or antigens. The method for its preparation and an immunization scheme of two doses are provided.

17 Claims, 11 Drawing Sheets

A

B it is started injecting small allergen doses and if allergic reactions do not appear, the dose is increased. The injections are administered with a weekly frequency at the beginning; then, doses are gradually increased until reaching a maintenance dose at monthly or semimonthly frequency. This treatment should be maintained for several years (WHO Position Paper. Allergen Immunotherapy: Therapeutic Vaccines against Allergic Diseases. Geneva, January 1998).

In spite of the method is regarded as relatively effective for some allergic diseases, the immunotherapy has been questioned due to safety reasons. During this treatment, the patient can suffer from severe anaphylactic reactions, which eventually can be even fatal. In addition, the high number of injections to administer, that can be about 100-200 in 3 years, constitutes a serious drawback for its practical application. Poor patient compliance and premature abandonment of the treatment are frequent causes of lack of expected effectiveness.

In recent years, it has been a great progress in the understanding of the mechanisms of the induction of IgE immune response in allergic subjects. IgE production by B-cells is driven by specific mechanisms of the Th2 immune cell response, and particularly, it is induced by an overproduction of IL-4 by Th2 cells. The Th2 cells are involved pathologically not only through their regulatory role (IL-4 induces the class switch to IgE in B-lymphocytes, mediated by a contact signal provided by T-cells), but also participate directly in the effector phase of the delayed type allergic inflammatory response and in the asthmatic chronic inflammation.

The exposure to environmental allergens, in addition to the own genetic predisposition, constitutes the leading phenomenon of the allergic sensitization process and causes the triggering of allergic reactions.

The immunological mechanism responsible for clinical improvement of the patients during allergen immunotherapy is not totally explained yet. Nevertheless, it is known that several immunological changes take place, linked to a long-term decrease of allergen specific IgE: there is a decrease of IL-4 and IL-5 secretion and increase of IFN-γ and IgG levels. These changes indicate a decrease of the Th2 response pattern, like a possible consequence of the induction of a non-pathogenic concurrent Th1 pattern (WHO Position Paper. Allergen Immunotherapy: Therapeutic Vaccines against Allergic Diseases. Geneva, January 1998).

The Th1/Th2 response patterns distinguish themselves firstly by the typical pattern of cytokines, secreted by Th-cells: namely IFN-γ and IL-2 by Th1 and IL-4 and IL-5 by Th2 (Mossman, T. R., Cherwinski, H., Bond, M. W., Giedlin, M. To, and R. L. Coffman. 1986. Two types of murine T helper cell clones. I. Definition according to profiles of lymphokine activities and secreted proteins. J. Immunol. 136: 2348-2357). On the other hand, it is also possible to determine the type of induced response determining serum Ig class/subclass profiles. Thus, murine Th1 pattern induces antibodies preferably of the IgG2 subclass (IFN-γ dependent), whereas Th2 induces IgE and IgG1 subclass (IL-4 dependent). In humans, Th1 is linked to IgG1/IgG3 antibodies and Th2 to IgE.

Although the onset and development of Allergy are caused by environmental factors, the fundamental role in the propensity of an individual to develop a Th2/IgE response is of genetic order (Holgate ST. Environmental Genetic and interaction in allergy and Asthma. J Allergy Clin Immunol 1999; 104:1139-1146). Therefore, the descendants of allergic parents will develop an allergic disease with a greater frequency than the children of non-allergic parents. This frequency has been estimated as 75, 50 and 25% if both parents, the mother or the father are allergic, respectively). That means that applying a diagnostic system to the parents, the behavior of an individual within the population, can be predicted with a high likelihood. Additionally, it is well known that the establishment of a pathological Th2 pattern occurs in the first 6-24 months of life. Environmental factors like exposition to bacterial infections can influence positively on the disease onset, inducing a Th1 pattern, which down-regulates the allergic Th2 pattern (Holt PG, Programming of Allergen Specific Th-memory during Childhood. Proceedings XVII International Congress of Allergology and Clinical Immunology. Sydney 2000. Allergy Clin Immunol International Suppl. 1, 2000 pp 83-85). These findings suggest the possibility of designing prophylactic anti-allergic vaccines, which could prevent the establishment of a Th2 response to allergens, in the early childhood. These vaccines could be based on Th1 adjuvants, which ideally should be effective during the breast-feeding period.

Several approaches have been attempted to improve allergen immunotherapy, aiming to reduce their negative aspects, preserving or extending their benefits. Particularly, it is known that several methods have been used in order to modify the allergens so that its allergenicity (i.e., its ability to be recognized by IgE antibodies) and ability to induce IgE antibodies following immunization could be reduced, as well as, to increase their immunogenicity (i.e. its capacity to induce a therapeutic or possibly protective response). Among them, there are physical methods by adsorption of allergens, creating a depot effect (adjuvants), or chemical methods aiming at modifying allergen molecules by means of covalent links with other compounds or between themselves.

Several physical agents have been used, among them: Tyrosine (Patent No. GB 1,377,074), Tyrosine Ester (U.S. Pat. No. 4,428,932); Liposomes (Patent Application WO 89/10753); Monophosforil Lipid A (MLA) (U.S. Pat. No. 5,762,943); Saponine (U.S. Pat. No. 4,432,969) and the traditional ones: Aluminum Hydroxide and Calcium Phosphate.

Among the chemical agents that have been used for allergen polymerization, are Formaldehyde (Marsch DG et al. Studies on allergoids from naturally occurring allergens. III Preparation of Ragweed pollen allergoids by aldehyde modification. J. Allergy Clin. Immunol. 1981; 68:449-59); Alginate (Corrado O J et al. Allergy 1989; 44:108-5) and Glutaraldehyde (Patent No. GB 1,282,163). Also, there have been used: MPEG (Dreborg et al. Crit Rev Ther Drug Carrier Syst. 1990; 6:315-65) and polysaccharide conjugates (European Patent Application No. EP 3497 008 A2).

These solutions could, in some cases (Eg. Glutaraldehyde polymerized allergens, Alum adjuvanted, Grammer et al., Modified forms of allergen immunotherapy, J Allergy Clin Immunol 1985; 44:108-15) increase the allergen-specific IgG titters in animal models. Nevertheless, the increase of this antibody class does not necessarily imply a clinical improvement of the patient, mainly if a parallel increase of IgE antibodies occurs. In fact, some IgG subclasses (IgG1 in mice and IgG4 in humans) are involved, also, in different allergic reactions, due to its ability to bind themselves, transitorily, to mast cell surface. On the other hand, clinical evidences in humans indicate that the increase of IgG antibodies is not correlated directly with clinical improvement, suggesting that these antibodies play only a secondary role in the regulatory mechanism, induced by the treatment (Rak S. Lowhagen O., Venge P. Bronchial The effect of immunotherapy on hyperresponsiveness and eosinophil cationic protein in pollen-allergic patients. J Allergy Clin Immunol 1988; 82:470-80 and Jutel M, Müller Or, Fricker M, Rihs S, Pichler W, Dahinden C. Influence of bee venom immunotherapy on degranulation and leukotriene generation in human blood basophiles. Clin Exp Immunol 1996; 12:1112-18)

Although, chemically modified allergens (so-called allergoids), has some advantages concerning the decrease of secondary adverse reactions during the treatment as compared to traditional allergen extracts, they do not produce a significant clinical improvement (Bousquet et al. J. Allergy Clin. Immunol. 1989; 84:546-56 and Grammer et al. J Allergy Clin Immunology 1985; 76:397-401). Another drawback of allergoids, used so far in clinical trials (modified by Glutaraldehyde or Formaldehyde), is the practical impossibility to obtain a standardized composition, since the final products are obtained by means of chemical reactions starting from allergen extracts, which are heterogeneous mixtures of polypeptides and other biomolecules. In these reactions, it cannot be avoided that molecular species with different degrees of polymerization or chemical modifications are formed, which can constitute unwanted, difficult to eliminate by-products.

The use of Aluminum Hydroxide has only managed to reduce the number of injections necessary to obtain the same effect that with the non-adjuvanted allergens, which is attributed to its depot and slow release effects. Nevertheless, it is known that this adjuvant stimulates IgE production, as much in animals as in humans, inducing a typical Th2 pattern, which could possibly reinforce the pathogenic allergic response, during its administration.

Calcium Phosphate and Tyrosine have also been used as adsorbents for creating a depot effect and slow release of the allergens. Nevertheless, these formulations have shown no significant advantages as compared to aqueous or Alum-adjuvanted extracts, regarding the effectiveness or safety of the treatment (Altintas D U et al. Comparison between the use of adsorbed and aqueous immunotherapy material in *Dermatophagoides pteronyssinus* sensitive asthmatic patients. Allergologie et Immunopathologie 1999; 27(6):309-317).

None of the existing at the present time, previously mentioned solutions could achieve completely effective immune modulation (expressed in inhibition or reduction of Th2 pattern or induction of Th1) neither in animals nor in humans, and no clinical effectiveness has been shown in patients, using a reduced number of injections.

The use of liposomes containing allergens has been described in the Patent Application WO 89/10753. It is regarded that liposomes, besides creating a depot and reducing allergenicity of the product, can influence the mechanisms of antigen presentation to the immune system, due to their lipidic and particulate nature (WHO Position Paper. Allergen Immunotherapy: Therapeutic Vaccines against Allergic Diseases. Geneva, January 1998). Nevertheless, this approach has several drawbacks that have hampered a wide introduction into the clinical practice. Among them: the lack of stability of these formulations and availability of a technology for inclusion of allergens into liposomes in a consistent way. The lack of stability of the liposome formulation during storage or administration to the patient has serious implications in the safety of the treatment, since the possible uncontrolled release of allergens from liposomes can cause severe anaphylactic reactions, similarly to allergens in aqueous form. Moreover, definitive evidences of the induction of an effective immune response, either that affects Th1/Th2 balance or that induces a non-pathological or protectogenic pattern, have not been obtained.

More recent approaches have tried to use allergen formulations with adjuvant inducers of Th1 response, such as Monophosforil Lipid A (MLA) (U.S. Pat. No. 5,762,943) and Heat Shock Proteins (HSP) also known as Mycobacterium Stress Proteins, which are described in the patent WO9823735. MLA, a detoxified variant of LPS, has been shown that reduces specific IgE and increases IgG levels, in experimental mice models. Nevertheless, it has not been demonstrated that it can effectively reduce the Th2 cellular component of the allergic response. Therefore, its use would be limited strictly to the allergic diseases for which the type 1 hypersensitivity mechanism is the main one, which would exclude asthma. Another major drawback is that, in spite of the fact that the toxicity of LPS has been attenuated, it has not been completely removed (Baldrick P et al. Vaccine 20, 2002 737-743), which could limit its use in small children. In the case of HSP, experimental evidences have not been provided, supporting that clinically relevant allergens mixed or conjugated to these proteins could produce a deviation of allergen-specific Th2 response, neither in animal models nor in humans.

The use of proteoliposomes derived from the outer membrane of Gram-negative bacteria has described for prophylactic vaccine formulations against infectious diseases, by Ruegg C L and cols. (Preparation of proteosome-based vaccines. J Immunological Methods 1990; 135:101-9); Lowell and cols. (Proteosome-Lipopeptide Vaccines Enhancement of Immunity for Malaria CS Peptides. Science 1988; 240: 800-2); also in the U.S. Pat. No. 5,597,572. In this last case, the main core is an outer membrane proteoliposome or vesicle (OMV) derived from *Neisseria meningitidis* serogroup B. It is regarded that its particulate structure, lipo-oligosaccharide traces (LPS) incorporated into the OMV; polysaccharide C; lipid composition and adsorption into Alum, are relevant for its proven immunogenicity and protectogenicity in humans.

In spite of containing LPS, this vaccine formulation does not cause toxic effects neither in humans nor in animals, which is attributed to the OMV peculiar structure and composition. On the other hand, the immunomodulator and adjuvant effect of LPS could be retained.

The anti-meningococcal vaccine, based on this proteoliposome, has been successfully applied in more than 50 million doses, demonstrating to be safe, non-reactogenic and effective to protect against *N. meningitidis* serogroups B and C. Moreover, it can be applied safely during the breast-feeding period. It has been shown that it is able to turn the T-independent Polysaccharide C antigen into a T-dependent one. This vaccine induces a preferential Th1 pattern in humans and animals, characterized by the induction of lymphoproliferation; anti-OMV IgG antibodies (subclass IgG1 in humans and IgG2a in mice); IFN-γ, IL-2 and IL-12, both at protein and mRNA level. It does not induce anti-OMV IgE, neither increases total IgE levels, nor IL-4, IL-5; both, at protein or mRNA level (Infect Immun. 2001, 69(72001):4502-4508). The response induced by the vaccine, as it is usual for the adaptive immunity, is specific to the bacterial antigens contained in the product, and therefore, there are no evidences of induction of an immune response towards well-known common allergens.

SUMMARY OF THE INVENTION

The object of the present invention is to obtain a pharmaceutical composition for therapeutic or prophylactic purposes, based on the use of bacterial proteoliposomes. This composition, once applied into allergic patients, is able to transform the allergic Th2 response, induced by the allergen, towards a cellular Th1 response. The invention also relates to the immunization scheme using this vaccine composition. It is also an object of the present invention, to provide a pharmaceutical composition able to prevent the onset and development of the allergic disease in children with atopic familial history.

This composition can contain one or several allergens, which can be coupled to the proteoliposomes or be administered simultaneously with it, inducing a therapeutic or protective immune response, specific to the allergen. This response is characterized by a decreased production of IgE antibodies as compared to the traditional immunotherapy, the non-induction of IL-5, as well as the induction of IgG1 antibody subclass (in humans) and IgG2a (in mice), and IFN-γ (in both). These features evidence the induction of a Th1 type immune response and the transformation of the allergenic Th2 response in to a cellular Th1.

It is still another object of this invention to provide the method for coupling allergen(s) to proteoliposomes and to other adjuvants, as well as to provide an appropriate pharmaceutical composition for its administration by parenteral route.

The novelty of the invention is firstly in the use of proteoliposomes derived from outer membrane proteins of Gram-negative bacteria and more specifically from *Neisseria meningitidis* B in conjunction with Aluminum Hydroxide. Thus, these proteoliposomes (alone or together with a polysaccharide) are coupled in a non-covalent or covalent way to one or several allergen proteins, adsorbed into the Aluminum Hydroxide gel, and, then, administered to allergic subjects.

It has a particular novelty, that this pharmaceutical composition induces a modulation of the specific immune response to the allergens included in it, towards a non-pathogenic and protective Th1 pattern, by using only two injections.

Another novel aspect is the prophylactic application of the pharmaceutical composition in the offspring of allergic parents or in early-diagnosed atopic individuals.

It is still novel, the procedure used in order to couple non-covalently the main components of the formulation and particularly: proteoliposomes to allergens, as well as the use of purified allergens for that purpose.

In the present invention, proteoliposomes or OMV, purified from Gram-negative bacteria culture, and particularly from *N. meningitidis* B, are used, as was described in the U.S. Pat. No. 5,597,572.

In the present invention, allergens of protein or glycoprotein nature are used preferably, although, it is possible also to use polysaccharide allergens. The allergens can be obtained from natural allergenic source materials, using well-known extraction and purification methods or can be obtained in recombinant form, by cloning and expression in microorganisms or higher organism cells. Alternatively, chemically synthesized polypeptides, according to the aminoacid sequence of the native allergens, can be used. Particularly, respiratory allergens are preferred: in the first place, from house dust mites belonging to Pyroglyphidae or Glyciphagidae families, especially belonging to *Dermatophagoides* or *Blomia* genus and specifically to *Dermatophagoides siboney*, *Dermatophagoides pteronyssinus* or *Dermatophagoides farinae* species. Purified allergens of these mite species are obtained preferably from any available commercial allergenic extract, which is subjected first to freeze-drying or concentration by ultrafiltration up to 10-100 mg/mL protein content, and next to saline precipitation in 50-100% ammonium sulfate solution. The pellet is reconstituted in aqueous solution and fractionated by means of gel-filtration chromatography, using matrixes of composite cross-linked dextran/agarose, such as SUPERDEX™ 75, or matrixes of cross-linked copolymer of allyl dextran and N,N-methylenebisacrylamide, such as: SEPHACRYL™ S-100, SEPHACRYL™ S-200 or SEPHACRYL™ S-300. The peak corresponding to 10-60 kDa Molecular Weight, is collected. This fraction contains mainly Group 1 (25 kDa glycoprotein: Der s 1, Der p 1, Der f 1) and Group 2 (15 kDa protein: Der s 2, Der p 2, Der f 2) major allergens. Alternatively, a separate purification procedure can be followed for each major allergen, preferably using anti Group 1 and anti Group 2 Mab-affinity chromatography; then, both components can be added to the formulation to be coupled to the proteoliposomes, or alternatively, be coupled separately to it.

The coupling of both basic components (allergen and proteoliposome) is performed by covalent or non-covalent links. The choice can be made taking into account the features of each particular allergen. For non-covalent coupling, the mite allergens are embedded into proteoliposomes at a ratio of 0.1-1 μg by 10 μg of proteoliposome. This coupling method takes advantage of the hydrophobic and lipophylic interactions between both components; the process is performed by means of mechanical agitation at 60 to 600 rpm rotation speed, during 30-60 minutes. The obtained mix can be administered directly in aqueous solution or adsorbed into Alum Hydroxide gel. In the last case, the allergen can also be adsorbed into the gel prior to be coupled to proteoliposomes or preferably, be added after adsorbing proteoliposomes into the gel. The amount of Alum Hydroxide should be 10 to 25 times the amount of proteoliposome, keeping the afore-mentioned proportion between allergen and proteoliposome content. The adsorption process into the Alum gel is performed by means of agitation at 60-600 rpm and pH values ranging from 6 to 8.

The efficacy of allergen adsorption in to Alum gel can be monitored using Mab-ELISA, specific to major allergens, E.g. anti-Der s 1 ELISA (Sewer et al. Int Arch Allergy Immunol 2000; 123:242-248) and anti-Group 2 ELISA (Heymann P W, Chapman M D et al J Allergy Clin Immunol 1989; 83:1055-1067)

The coupling of allergen to proteoliposome can be performed also by a covalent link, using a cross-linker or spacer, which can be coupled to the available amino groups on the proteoliposome, followed by the coupling of the spacer Maleimide group to the free Sulfhydryl (SH) groups on to the allergen molecule. Such free SH groups are present in the mite major allergen proteins (Group 1 and 2), nevertheless, they can also be induced in other allergens by reducing the disulphide bridges or by derivatization of proteins by well-known chemical methods. The obtained conjugates are later purified by dialysis or ultrafiltration and finally by gel-filtration chromatography (Sephacryl S-300 or Superdex 200) in order to remove the conjugation reagents, as well as the non-bound allergens. Allergen molecules must constitute between 1 and 10% of the total mass of the conjugate, in order to induce a suitable immune response. Conjugates are administered by injectable route in an appropriate aqueous excipient or adsorbed into Alum Hydroxide gel or another suitable depot adjuvant.

The present invention also includes the conjugation, by the method described before, of lipofilic residues, such as bipolar fatty acids of 16 to 20 carbons, to the allergens, aiming to facilitate its non-covalent incorporation into the proteoliposome.

Alternatively, the vaccine composition may include other antigens, which do not affect the induced cellular pattern and strengthen the expected response to the allergen. Polysaccharides, and particularly polysaccharide C from *N. meningitidis*, can be used for this purpose. They are added in a non-covalent form to the formulation in a proportion of 0.5 to 4 times the amount of proteoliposome.

The present invention also comprises the use of allergens of polysaccharide nature. In that case, the allergens are added to the formulation in the same way as described for *N. meningitidis* polysaccharide C.

Unexpectedly, the administration of this vaccine composition by parentheral route in only two doses, induced, not only a specific Th1 response to the proteoliposome antigens, as was previously known, but also a similar Th1 response directed against the allergens included in the formulation. Surprisingly, this Th1 response prevails, in spite of using Alum Hydroxide in the formulation, preserving the depot effect. This response is characterized by a cytokine pattern with high levels of IFN-γ, and no induction of IL-5, also, by induction of allergen-specific IgG2a antibodies and reduction of IgE and IgG1 antibodies in mice. The administration of this composition does not affect a preexisting response against the bacterial antigens, induced by prior immunizations.

The Proposed Solution has the Following Advantages:

The immunological effect induced by this vaccine composition counteract both: the anaphylactic type I hypersensitivity response (reduction of IgE and IgG1), and the delayed type inflammatory and chronic allergic reactions (IL-5 reduction), which makes it effective in the treatment of asthma. The therapeutic effect is attributed to the presentation of allergens to the immune system in a non-allergenic context, and it is achieved in a reduced number of injections and in a shorter time as compared to traditional immunotherapy with allergen extracts. Such effect is used advantageously not only in the treatment of allergic patients, but also it allows to prevent the disease development in individuals with an early allergic state or to prevent the onset of new allergic sensitizations to other allergens.

The immunological effect of proteoliposomes as an immune-modifier adjuvant is effective and safe in the first months of life, during the breast-feeding period. It makes possible the administration of the vaccine in children at this age with a prophylactic purpose, before that the disease has appeared and developed. It is particularly useful for children with allergic familial history and therefore with a high probability of being so.

The adsorption of the active components into a depot adjuvant, specifically into Aluminum Hydroxide, reduces the allergenicity of the formulation (i.e. the capacity of IgE binding), in more than 10 times in relation to a similar dose of aqueous allergen. This implies a considerable reduction of risk of severe anaphylactic reactions during its administration. In addition, the adsorption into the gel contributes to extend the shelf-life stability of the formulation by decreasing the kinetics of the chemical reactions that can possibly cause degradation of the active components.

The use of purified allergens and particularly of purified mite allergen of the Dermatophagoides genus, including Group 1 and 2 allergens, facilitate the standardization of the product composition. Then, it is possible to determine and fit accurately the allergen content in the formulation and to assess the efficacy of its coupling to the proteoliposome and adsorption into Aluminum Hydroxide gel. In addition, in the case of covalent coupling, it is possible to easily separate unwanted by-products (such as the allergen-allergen polymers) from the active compound (proteoliposome-allergen conjugate) thanks to the big difference in Molecular Weight between both components. This separation can be performed using commercially available size-exclusion chromatography. The technology can be applied to allergens of different nature, being possible to use several allergens in a same formulation.

Another advantage is the lack of toxicity of the product, in spite of containing small amounts of LPS, which, on the other hand, retains their immunogenic effect. That makes it appropriate for a safe administration to humans and particularly to small children.

Proteoliposomes also turn T-independent antigens, such as carbohydrates, into T-dependent antigens. This feature can also be advantageously applied to allergens of polysaccharide nature, such as CCD.

The present invention will be described through the following specific examples.

EXAMPLE 1

Obtaining and Purification of Mite Allergens

The allergens are obtained from whole mite culture, which contains dead mites, scales, fecal particles, as well as low molecular weight culture media ingredients. The allergens are extracted in one of the following solutions: ammonium bicarbonate, sodium bicarbonate, phosphate buffered saline or saline, with a pH value close to the physiological one. Crude extract is clarified by centrifugation and filtration, and low molecular weight components are removed by means of gel-filtration chromatography (Sephadex G-25) or diafiltration (cutoff value: 5-10 kD) or both. Then, the product is concentrated by ultrafiltration and freeze-dried to assure its stability. In order to further purify the allergens, the freeze-dried extract is resuspended in to aqueous solution and subjected to salting-out precipitation in 50-100% ammonium sulfate solution. The pellet is resuspended again in water and fractionated by gel-filtration chromatography using Superdex 75. The intermediate peak is collected, which corresponds to the 10-60 kDa molecular weight range. This fraction mainly contains Group 1 (25 kDa) and Group 2 (15 kDa) major allergens. Finally, the collected fraction is freeze-dried again to be reconstituted in an appropriate concentration to be coupled to the proteoliposome.

EXAMPLE 2

Obtaining the Proteoliposome

It is started from a *N. meningitidis* B culture. The biomass is harvested by centrifugation and subjected to an extraction process with detergent, enzymes and ultrasonic treatment. The cellular debris is removed by centrifugation and the supernatant is subjected to a nuclease digestion process in order to eliminate nucleic acids. The extract is recovered by means of ultracentrifugation, resuspended into a detergent solution and purified by removing the rest of low and medium molecular weight components, using molecular exclusion chromatography. The proteoliposomes thus obtained, contains less than 10% of nucleic acids and about 10% LPS, embedded in their structure; but none in a free form. Optionally, the capsular polysaccharide, obtained from *N. meningitides* serogroup C according to Gold and Gotschlich (Gold et al., 1969-1970, WHO Bull. 45: 279-282 and Gotschlich et al., 1969, J. Exp. Med. 129: 1349-1365) is added, at a proportion of 0.5 to 4 times the proteoliposome content. Optionally, Aluminum Hydroxide can be added as an additional adjuvant at a rate of 10 to 25 times the amount of Proteoliposome. The final pH value is kept at 7.0±0.4. The adsorption of the proteoliposome-polysaccharide complex in to Alum gel is greater than 80% and LPS content below 6% is guaranteed. LPS is embedded into the proteoliposome, which allows an adequate presentation to the immune system, reducing the possibility of unwanted toxic reactions. Thiomersal can be added as preservative to a final concentration of 0.005-0.02%. The final product is subjected to several biological and physical-chemical quality control assays.

EXAMPLE 3

Determination of the Allergenicity (IgE Binding Activity) of the Formulation Adsorbed in to Aluminum Hydroxide The allergenic activity, expressed as the binding capacity of human IgE antibodies, was determined by means of IgE-inhibition ELISA. This assay determines the ability of the sample solution to inhibit the IgE binding to solid phase coated allergen. In this case, the sample formulation is the *D. siboney* purified allergen according to Example 1, mixed with proteoliposomes obtained according to Example 2, and adsorbed into Aluminum Hydroxide gel. The initial Der s 1 allergen concentration is 4 μg/mL and the allergenic activity: 400 BU/mL (BU: Biological Units according to the definition of Nordic Guidelines for the Registration of Allergenic Products, 2nd Edition. 10 000 BU/mL are equivalent to 10 mg/mL Histamine HCl in the Skin Prick Test)

ELISA is carried out according to the following procedure. Polystyrene microplates are coated with the Reference Allergen Extract. Non-specific binding sites are blocked with PBS-BSA 1%. Next, the inhibition of the IgE serum pool is performed, by incubating the serum with increasing amounts of the allergen sample and the Reference, in parallel. Non-inhibited IgE is captured by the allergen coated on to the plate. After washing out non-specifically bound antibodies, the detection of the IgE, bound to the allergen is carried out, adding Peroxidase labeled anti-IgE MAb. After adding a suitable chromogenic substrate, the color intensity of the reaction product is measured, using an ELISA plate reader. The parallel lines statistical method is used for the analysis and interpretation of the results. Reference and sample inhibition curves are built, and a linear regression analysis is performed, verifying the parallelism between each sample line and the Reference line. Finally, the relative potency is calculated as inverse log of the horizontal distance between the parallel lines.

In the analysis of the given sample, the following results were obtained:

Allergenic activity: 21.2 BU/mL (IC95% 13.6-32.4). This value represents only 5.3% of the initial activity of the allergen in aqueous solution.

EXAMPLE 4

Determination of the Scheme and Dosage Showing Less Induction of Total IgE

For determination of the immunization scheme (time between doses) and allergen concentration, Balb/c mice were administered by intramuscular route with two immunizations at weeks: 0 and 2 (short scheme) or 0 and 4 (long scheme) with Allergen (Al)+Alum (A) at concentrations of 1 or 5 μg/mouse of Der s 1. In the short scheme, the animals were bled at weeks 0, 2 and 5, and in the long scheme at weeks 0, 4 and 7. Total IgE level in serum pools was determined by ELISA.

As it can be observed in FIG. 1, the short scheme induces an IgE response significantly smaller than the long scheme. On the other hand, the lower allergen concentration (1 μg)

failed to induce IgE in all the schemes. For that reason, the following experiments were carried out using the short scheme and an allergen dose around 1 µg/mouse.

In order to determine more accurately the dose, Balb/c mice were administered again by intramuscular route with two immunizations at weeks 0 and 2 and were bled at weeks 0 and 4. Group I received the adjuvant mix (consisting of proteoliposome+serogroup C *N. meningitidis* polysaccharide+Al(OH)$_3$, labeled as "Va" throughout the rest of examples and figures). Groups II, III and IV received Al(OH)$_3$+allergen at the following doses: 0.5; 1.25 or 2.5 µg/mouse, respectively. Total IgE level in serum pools was determined by ELISA. As it can be observed in FIG. 2, IgE did not show any significant increase in any of the evaluated groups.

EXAMPLE 5

No Effect of Allergen Incorporation on to Proteoliposome-Specific Response and Modulation of Allergen-Specific IgG Subclass Response For the determination of the allergen effect on the response towards the proteoliposome antigens, Balb/c mice were administered by intramuscular route with two immunizations at weeks 0 and 2. Group I received Va. Groups II, III and IV received 0.5; 1.25 and 2.5 µg/mouse of Allergen+Va, respectively. The bleeding was made at 0, 15 and 35 days, after the first immunization. Proteoliposome and allergen-specific IgG subclass responses were determined by ELISA.

As can be observed in FIG. 3, high IgG anti-proteoliposome titters were detected, and surprisingly, no effect was noted due to incorporation of the allergen. No effect was also detected in IgG subclass response (FIG. 4). High IgG2a titters are an expression of a preferential Th1 response, induced by this adjuvant. FIG. 5 shows the stimulation of different allergen-specific IgG subclasses. It can be noted the increase of IgG2a levels at lower allergen concentrations, and particularly at 1.25 and 0.5 µg. The induction of IgG2a response to the allergen reflects that the adjuvant was able to modulate the Th2 response towards Th1.

EXAMPLE 6

Production of IFN-γ and No IL-5 by Spleen Cells of Immunized Mice, Following In Vitro Challenge with the Proteoliposome or the Allergen. Correlation of the cytokine production with the allergen-specific IgG subclass response. Comparison between the adjuvant formulation: proteoliposome+polysaccharide C+Al(OH)$_3$ and Al(OH)$_3$ alone.

For the determination of Th1 (IFN-γ) and Th2 (IL-5) cytokine response, Balb/c mice were immunized with two doses at weeks 0 and 2. Group I received Va. Groups II, III and IV received 0.5; 1.25 and 2.5 µg/mouse of Allergen+Va, respectively. Group V received an initial dose of Va and a second dose of 0.5 µg Allergen+Va. The animals were sacrificed 7 days after the last dose. The spleen was removed and processed by routine techniques and the cells were cultured in presence of proteoliposome or allergen. After 72 hours, the culture supernatants were collected and processed by ELISA for the determination of IFN-γ and IL-5.

Proteoliposome challenge of the cell culture induced IFN-γ production in all the groups, which is in correspondence with the known Th1 pattern induced by this adjuvant. However, in the groups immunized with 0.5 µg allergen dose, the IFN-γ production was surprisingly reinforced, when either two allergen injections were administered (Group II) or when a previous dose of Va and a single allergen injection were used (Group V, FIG. 6). Surprisingly, the allergen challenge also induced IFN-γ response in all the groups. Unexpectedly, this response was higher in groups immunized with 0.5 µg of allergen for both variants: two allergen injections or only one allergen injection with a previous Va administration (FIG. 7). IL-5 response was not detected following proteoliposome or allergen challenge. These results reflect the modulation by the adjuvant of the allergen-induced Th2 pattern, towards a Th1 pattern.

In order to determine the allergen-specific IgG and IgG subclass antibodies, another similar experiment was carried out. The mice were immunized following the same design described above, but using, in addition, allergen adsorbed into Al(OH)$_3$, alone. Bleeding was performed at 0, 15 and 35 days after the first immunization. Serum IgG response was assessed by ELISA. Allergen-specific IgG response was significantly higher when the Va adjuvant was used, as compared to Al(OH)$_3$. Surprisingly, the differences between both adjuvants were higher with the lowest allergen doses: 0.5 and 1.25 µg. However, the highest allergen-specific IgG response was achieved with the highest allergen dose for both adjuvants (FIG. 8). The predominant IgG subclass was IgG1 for all adjuvants and combinations. However, IgG2a subclass was induced with all compositions containing Va, whereas only slightly positive values were obtained with Al(OH)$_3$ at the two highest allergen doses (2.5 and 1.25 µg). On the contrary, surprisingly, the highest difference regarding IgG2a response between both adjuvants, was found with the lowest allergen dose (0.5 µg). In that case, the values were found to be negative for Al(OH)$_3$ and positive for Va (FIG. 9).

EXAMPLE 7

Determination of the Induction and Functionality of Allergen-Specific IgE

For the determination of allergen-specific IgE response, Balb/c mice were immunized with two doses at weeks 0 and 2. Group I received Al(OH)$_3$. Group II Va. Groups III and IV received 1 and 5 µg of allergen+Al(OH)$_3$, respectively. Groups V and VI received 0.5; 1.25 and 2.5 µg of allergen+Va. The animals were bled at 0, 15 and 35 days after the first immunization. The IgE response was evaluated in male Wistar rats by the Passive Cutaneous Anaphylaxis (PCA) method by a qualitative and semi-quantitative assessment. The response variables were expressed in terms of time and serum dilution that resulted positive, and in spot density arbitrary units.

Sera were extracted at days 0 (To), at the time of the second dose (T15) and 14 days after the second dose (T35). As it can be observed in Table 1 (Intensity of the reaction spots in PCA and last positive serum dilution), the last positive dilutions for groups V to VII (when the vaccine composition was used) are lower than in groups III and IV (Alum). The same happens with the optical densities. This indicates an important reduction in the allergen-specific IgE response. No response was observed in the negative controls (I and II).

In the negative control groups (I and II), the response values were negative. In the group III a positive value was observed at 35 days, with an intensity of 10660, which was detectable up to a 1:16 dilution. Group IV resulted positive starting from the first dose (15 days) with an intensity of 9345, detectable up to 1:8 dilution. At 35 days, a powerful response with an intensity of 39843, detectable up to 1:32 dilution, was observed. By the opposite, surprisingly, in the groups administered with Va, the allergen-specific IgE response was very low, only found at 35 days, showing low intensities and was detectable only at low dilutions. It can be noted, that with the lowest allergen dose (0.5 µg), it was only detected a minor response using undiluted serum (1:1), which disappeared when the serum was diluted 1:2 (FIG. 10 and Table 1). These results showing lower IgE induction with the Va adjuvant as compared to plain Al(OH)$_3$, and using the lowest allergen doses, agree with the results of the previous Examples, where total IgE was found to be lower and IFN-γ and IgG2a, higher.

TABLE 1

| Group | Immunization | Positivity, days after 2nd dose | Spot density (arbitrary units) | Last positive dilution |
|---|---|---|---|---|
| I | Al | — | 0 | — |
| II | Va | — | 0 | — |
| III | 1 µg A + Al | 35 | 10660 | 1:16 |
| IV | 5 µg A + Al | 15* | 9345 | 1:8 |
|  |  | 35 | 39843 | 1:32 |
| V | 0.5 µg A + Va | 35 | 1245 | 1:1 |
| VI | 1.25 µg A + Va | 35 | 4054 | 1:4 |
| VII | 2.5 µg A + Va | 35 | 4574 | 1:8 |

Legend: "Al", Al(OH)$_3$;; "Va", adjuvant mix consiting of Proteoliposome, Polysacharide C and Al(OH)$_3$; A,, Allergen and "*", days after de first dose.

EXAMPLE 8

Covalent Coupling of the Allergen to the Proteoliposome

The covalent coupling by chemical conjugation can be performed by some of the known methods, for example, the methods described in U.S. Pat. No. 4,695,694 and U.S. patent application Ser. Nos. 362,179; 555,558; 555,974; 555,966 and 555,339. The preferred methods use homobifuntional reagents like Glutaraldehyde or Succinic Anhydride, which couple both molecules through the free amino groups. These free amino groups can be found in allergen proteins and in the proteoliposome, particularly in Lysine residues. In addition, heterobifuntional reagents are used, preferably N-Hydroxisuccinimide-Maleimide Esters (such as MBS, MPS, SMPB, GMBS, EMCS). The reaction in this case is carried out, first, through the coupling of the cross-linker to available amino groups on the proteoliposome, followed by the coupling of the cross-linker Maleimide group to the free Sulfhydryl groups on to the allergen molecule. An example of conjugation of *Dermatophagoides siboney* purified allergen to proteoliposome, using the Glutaraldehyde method, and an example of the induced response, following immunization in mice with the conjugate, are presented below.

Conjugation: Purified allergen protein according to Example 1 was added to a 200 µg/mL proteoliposome PBS solution, pH 7.0, at a final allergen concentration of 20 µg/mL. One volume of Glutaraldehyde 0.4% was added, and it was shaken during 1 hour. The reaction was stopped adding 25 mol/L Glycine (final concentration); then, pH was adjusted to 7.0-7.8. The not bound Glutaraldehyde was removed by gel-filtration in a Sephadex G25 column. In order to further purify the conjugate, to remove remained free allergen, the product was passed through Sephacryl S-300 chromatographic column with the previous addition of Sodium Deoxycholate detergent up to 1% final concentration. The first peak was collected, which corresponds to the exclusion volume of the matrix. Later the detergent was removed by dialysis against PBS. The obtained product was concentrated 10-fold by membrane Ultrafiltration (Amicon, USA) with a 10 000 KDa cut-off value. Der s 1 content in the conjugate was measured by sandwich ELISA using allergen-specific monoclonal antibodies. The concentration was adjusted, by dilution with PBS to an appropriate value for the adsorption process: 10 µg/mL. Finally, the product was sterilized by 0.2 µm membrane filtration.

Adsorption process: Equal volumes of Aluminum Hydroxide 1.2 mg/mL and conjugated allergen solution 10 µg/mL were mixed in PBS pH 7.0. The mixture was gently shaken at 200 rpm, during 30 min. The protein adsorption into the Aluminum gel was checked by monitoring the supernatant absorbance at 280 nm, rendering a value higher than 90%.

Immunization: Three groups of Balb/C mice (7 mice each) were immunized with two doses of allergen in PBS solution ("A"), or allergen-proteoliposome conjugate in PBS ("PLS-A"), or Allergen-proteoliposome conjugate in Aluminum Hydroxide ("[PLS-A]Alum"), respectively. The Der s 1 allergen concentration was 5 µg/mL for all the variants. The injections were administered by intraperitoneal route, at weeks 0 and 4. Mice were bleed at the beginning of the experiment (0) and at weeks 4 and 8.

Results: Total IgE and allergen-specific IgG, as well as, IgG1, IgG2a and IgG2b subclasses serum antibodies, were determined by ELISA. In addition, allergen-specific IgE response was determined, using the Passive Cutaneous Anaphylaxis (PCA) method, in Wistar rats. The results regarding the antibody response are shown in FIG. 11. It can be noted, that in general, the variants containing the conjugate induce an IgG response significantly higher than the allergen alone. This is also valid for all IgG subclasses: IgG1, IgG2a and IgG2b. However, total IgE response was lower for the variant containing the conjugate in PBS solution (i.e. without Aluminum Hydroxide). In addition, the PCA results showed that this variant did not induce any detectable allergen-specific response (higher than the Negative Control), whereas both the free allergen and the conjugate adsorbed into Aluminum gel did induce detectable responses at 1:1 and 1:10 dilutions, respectively.

EXAMPLE 9

Formulation with Several Allergens

The formulation of different allergens in one vaccine composition can be carried out by non-covalent coupling (by mixing and adsorption into the Aluminum Hydroxide gel) or by covalent coupling, according to Example 8, with further adsorption into the Aluminum gel. In that case, each allergen is conjugated separately to the proteoliposome, and finally formulated altogether. In the present example a preparation of a non-covalent formulation of three allergens from different mite species, common in tropical regions (*Dermatophagoides pteronyssinus, Dermatophagoides siboney* and *Blomia tropicalis*), is exposed.

The allergens of said mites are prepared separately according to Example 1. In the case of *Blomia* the whole freeze-dried allergen extract is used, without fractionation. The content of Der p 1, Der s 1 and Blo t 5 major allergens is determined using Mab-ELISA. Total allergenic activity is determined by IgE-inhibition ELISA, according to Example 3. Freeze-dried allergens were resuspended in PBS pH 7.0 at a concentration of 20 µg/mL (for Der p 1 and Der s 1) or 10 µg/ml (for Blo t 5) and sterilized by 0.2 µm membrane filtration, rendering an allergenic activity of 4000 BU/mL. The proteoliposome was added to each allergen separately at a final concentration of 200 µg/mL. The solutions were homogenized during 30 min with gentle agitation at 150 rpm. Then, equal volumes of Aluminum Hydroxide 2 mg/mL in PBS pH 7.0 were added to each allergen solution and mixed, with gentle agitation during 60 min at 150 rpm. The adsorption of proteins to the Aluminum gel was checked by monitoring the supernatant absorbance at 280 nm. Finally, the three individual allergens products were mixed, with gentle agitation during 10 minutes. It was demonstrated that the allergens and the proteoliposome were almost completely adsorbed into the gel by assaying the suspension supernatant for Der p 1, Der s 1 and Blo t 5 content by ELISA (INDOOR Biotech, UK), and by the Lowry method for protein content determination. The residual (not adsorbed) allergenic activity was determined according to Example 3. It was obtained more than 90% allergen adsorption and a reduction of the Allergenic activity to less than 20%.

Two 0.5 mL doses of the formulation (total allergen content: 3.33 µg Der s 1 and Der p 1, 1.17 µg Blo t 5) were administered to Balb/c mice with a three weeks interval by intraperitoneal route. Allergen-specific IgG antibodies were determined by ELISA, after 7 weeks from the beginning of the immunization scheme. It was found a balanced antibody response to all the allergens, in a proportion of about 2:2:1, to *D. pteronyssinus, D. siboney* and *Blomia tropicalis*, respectively. The observed IgG levels were, as average, 80% higher than the values obtained for the immunization with the allergen mixture in PBS.

BRIEF DESCRIPTION OF THE DRAWINGS

The following symbols were used throughout the FIGS. 1 to 11:
  Va: adjuvant consisting of Proteoliposome+Polysaccharide from *Neisseria meningitidis* serogroup C+Aluminum Hydroxide gel;
  A: allergen; the figure preceding or following "A" indicates the used dose level, in µg.
  Al: Aluminum Hydroxide gel

Figure 1:
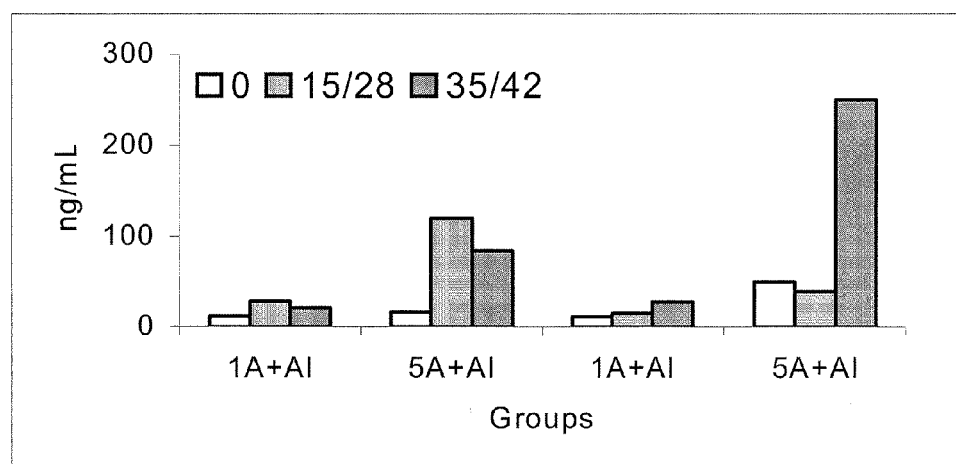
FIG. 1 shows that the short scheme (0-14 days) induces less total IgE that the long scheme (0-28 days). Bleedings were performed at 0, 15 and 35 days after the immunization in the short scheme and at 0, 28 and 35 days in the long scheme. Allergen doses: 1 and 5 µg/mouse. As it can be observed, the IgE response is higher in the group immunized with 5 µg using the long scheme than using the short one, after the second injection. In fact, the secondary response in the group with identical concentration with the short scheme has a tendency to decrease.
Figure 2:
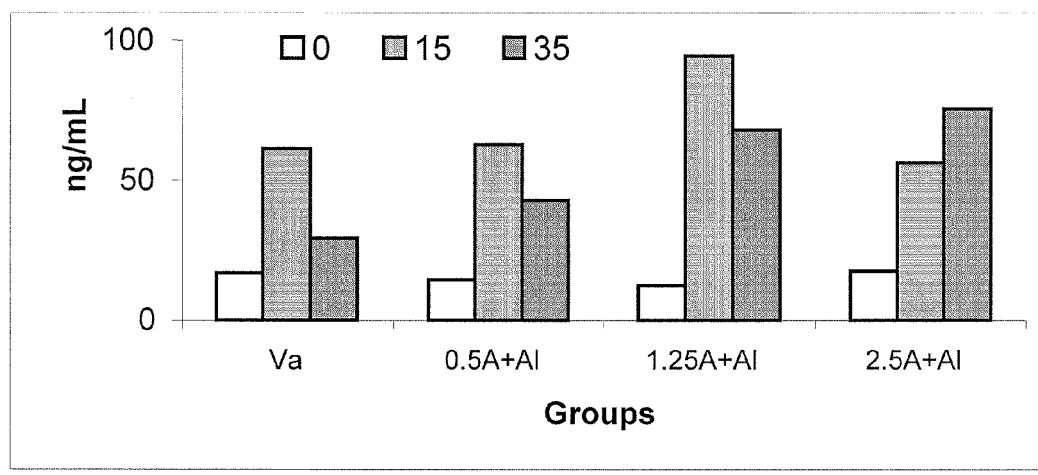
FIG. 2 shows the allergen concentration that produces less induction of total IgE. Bleeding: at 0, 15 and 35 days after the immunization. Allergen doses: 0.5; 1.25 and 2.5 µg/mouse. As can be noted the induction of total IgE by the 0.5 µg allergen dose is similar to the adjuvant control (Va). The other two allergen concentrations (1.25 and 2.5) do increase total IgE level.
Figure 3:
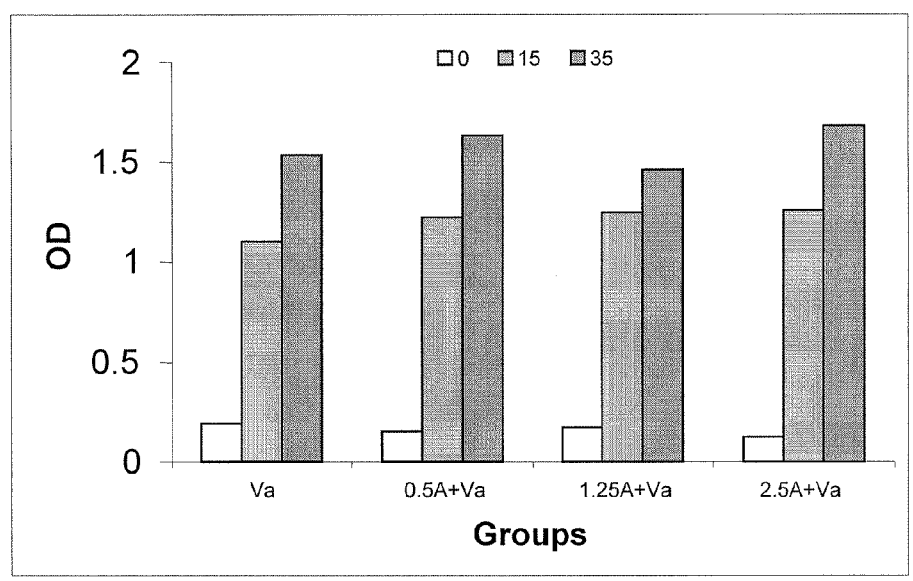
FIG. 3 shows how the Inclusion of the allergen does not affect the proteoliposome-specific IgG response. Bleedings: at 0, 15 and 35 days after the immunization. Allergen doses: 0.5; 1.25 and 2.5 µg/mouse. It can be noted that the inclusion of the allergen in to vaccine composition does not affect the IgG response to the proteoliposome antigens, neither after the first nor second dose as compared with the administration of the adjuvant mix without allergen (Va).
Figure 4:
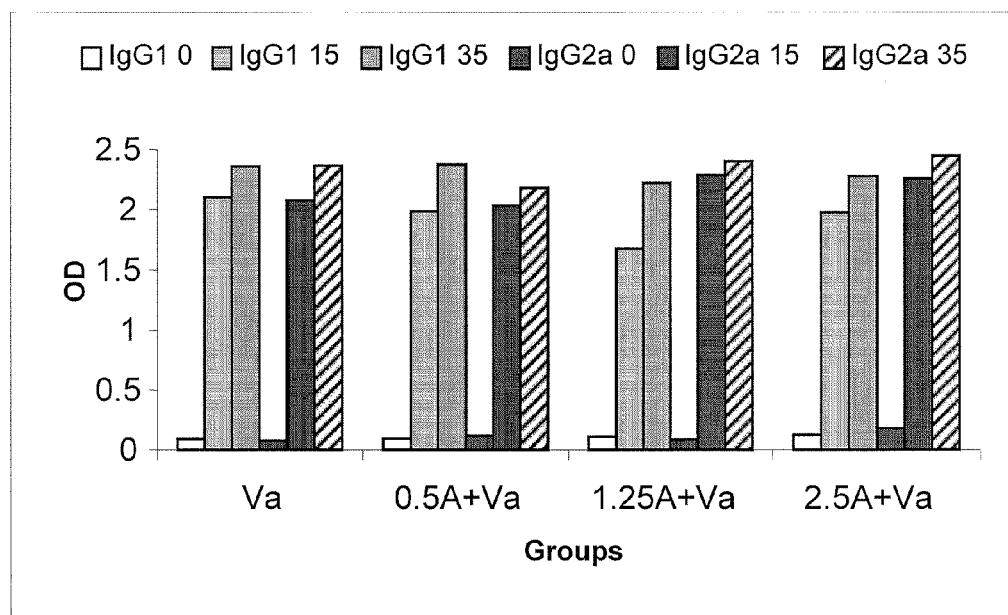
FIG. 4 shows that Inclusion of the allergen does not affect the proteoliposome-specific IgG subclass response. Bleedings: at 0, 15 and 35 days after the immunization. Allergen doses: 0.5; 1.25 and 2.5 µg/mouse. The immunization with the vaccine composition including the allergen, keep unchanged the proteoliposome-specific IgG subclass pattern as compared to the adjuvant mix alone (Va).
Figure 5:
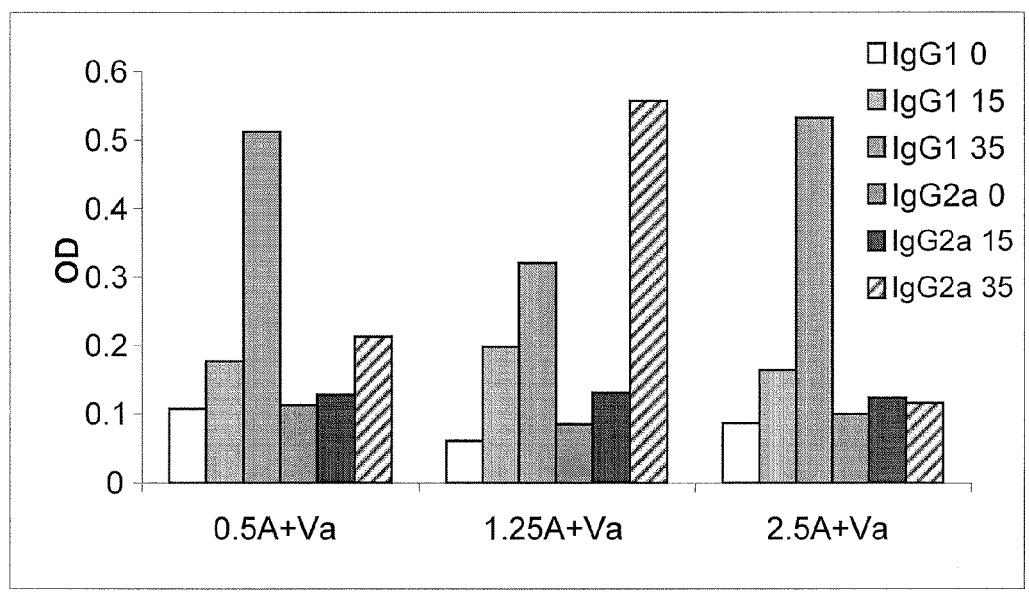
FIG. 5 shows how allergen specific IgG2a antibodies were induced by low allergen concentrations. Bleedings: at 0, 15 and 35 days after the immunization. Allergen doses: 0.5; 1.25 and 2.5 µg/mouse. Chart A shows the results using Va and Chart B, using only Proteoliposome (P)+Aluminum Hydroxide (Al). The two lowest allergen concentrations (0.5 and 1.25) induced an IgG2a response.
Figure 5:
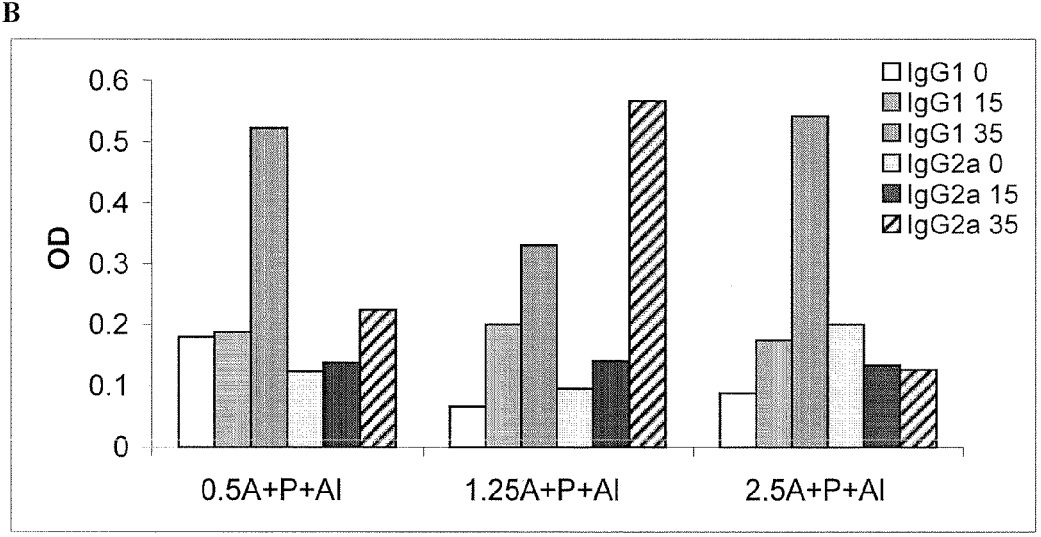
Figure 6:
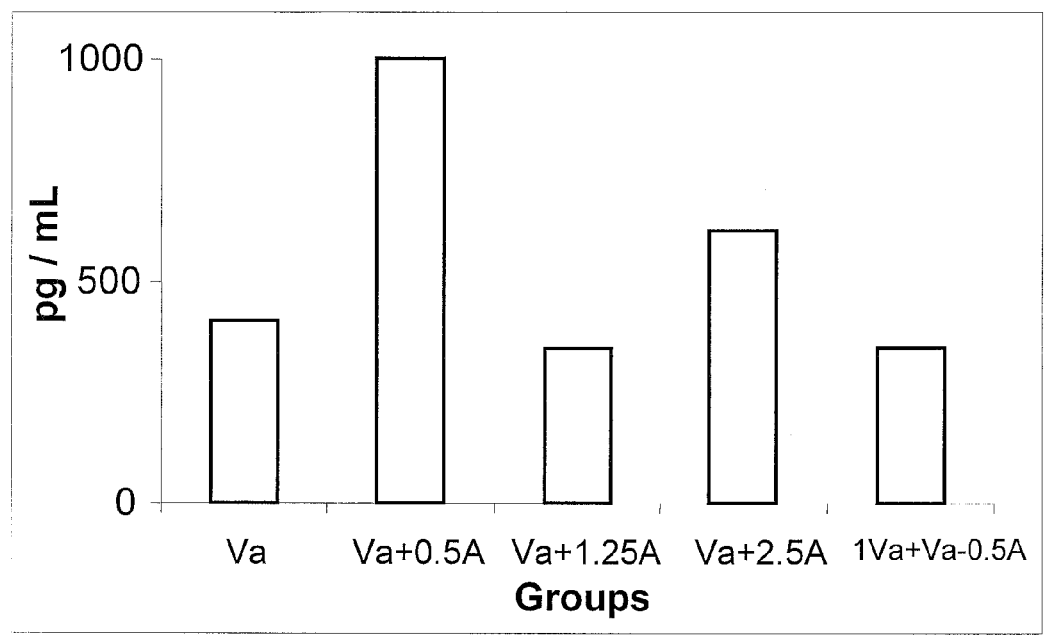
FIG. 6 is referred to the determination of the proteoliposome-induced IFN-γ production. Spleen cells were extracted 7 days after the second immunization (week 2). Allergen doses: 0.5; 1.25 and 2.5 µg/mouse. "1Va+Va−A0.5" means: initial injection with Va and a second dose with Va+0.5 µg allergen. The lowest allergen concentration increases the proteoliposome-induced IFN-γ production.
Figure 7:
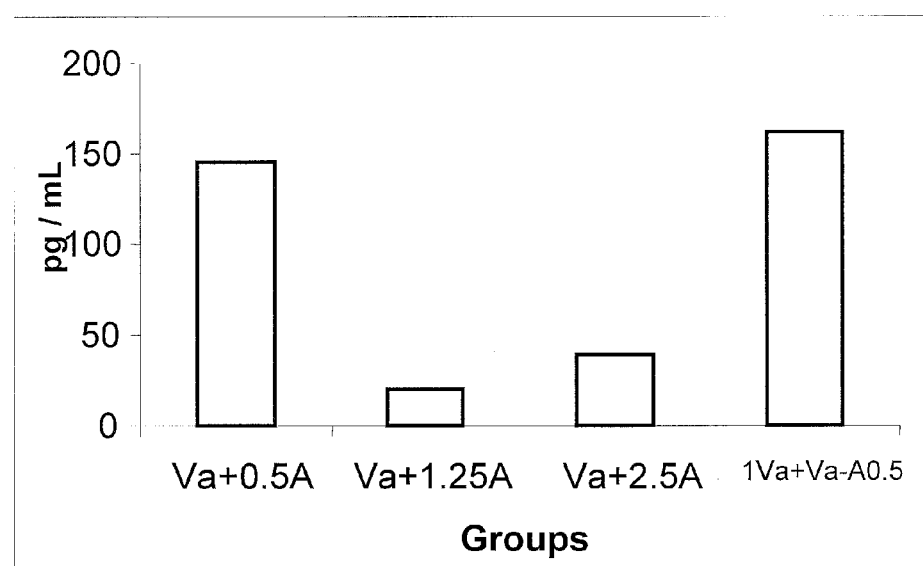
FIG. 7 is referred to the determination of the allergen-induced IFN-γ and lack of influence of a previous dose of the adjuvant. Spleen cells were extracted 7 days after the second immunization (week 2). Allergen doses: 0.5; 1.25 and 2.5 µg/mouse. "1Va+Va−A0.5" means: initial injection with Va and a second dose with Va+0.5 µg allergen. Allergen-induced IFN-γ production was observed for all allergen concentrations, but it was higher at the lowest concentration value. A previous injection of the adjuvant mixture does not affect this response.
Figure 8:
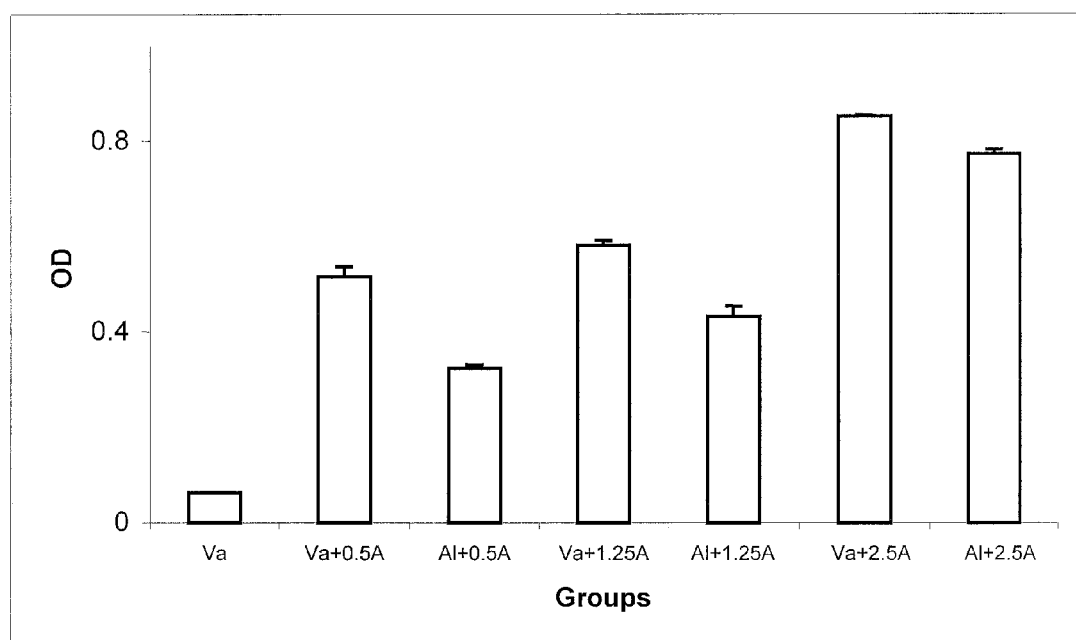
FIG. 8 shows that the lowest allergen doses induce greater differences of allergen-specific IgG response between the vaccine composition and Alum Hydroxide. Sera were extracted 14 days after the second dose. Injections were administered at days 0 and 27. Allergen doses: 0.5; 1.25 and 2.5 µg/mouse. It can be observed that, the lowest doses (0.5 and 1.25) induced greater increases in the allergen-specific IgG response, than the highest dose.
Figure 9:
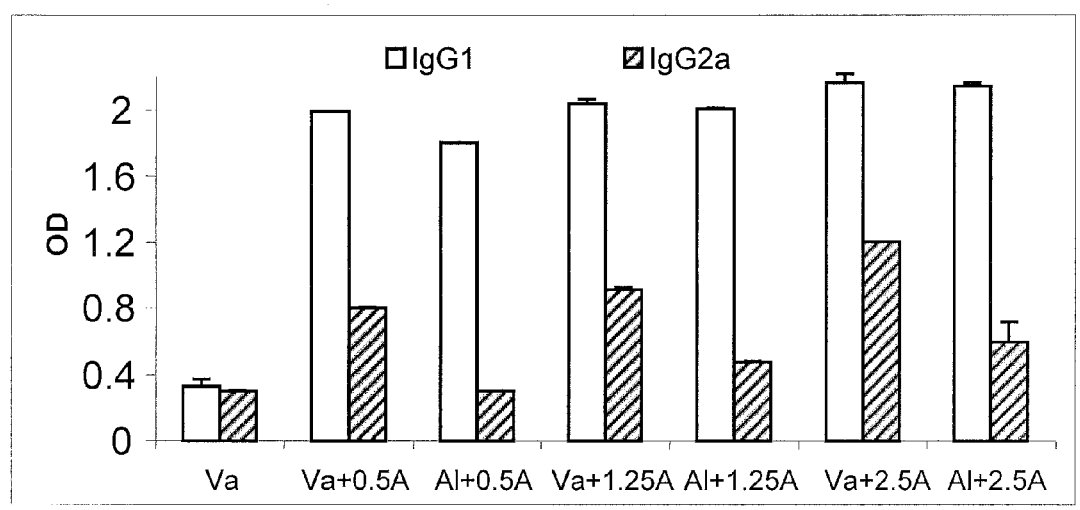
FIG. 9 is referred to the induction of allergen-specific IgG2a. Sera were extracted 14 days after the second dose. Injections were administered at days 0 and 27. Allergen doses: 0.5; 1.25 and 2.5 µg/mouse. It can be observed that, all the variants containing the adjuvant mix (Va) induced a significant allergen-specific IgG2a response as compared to the variants containing only Alum-adsorbed allergen.
Figure 10:
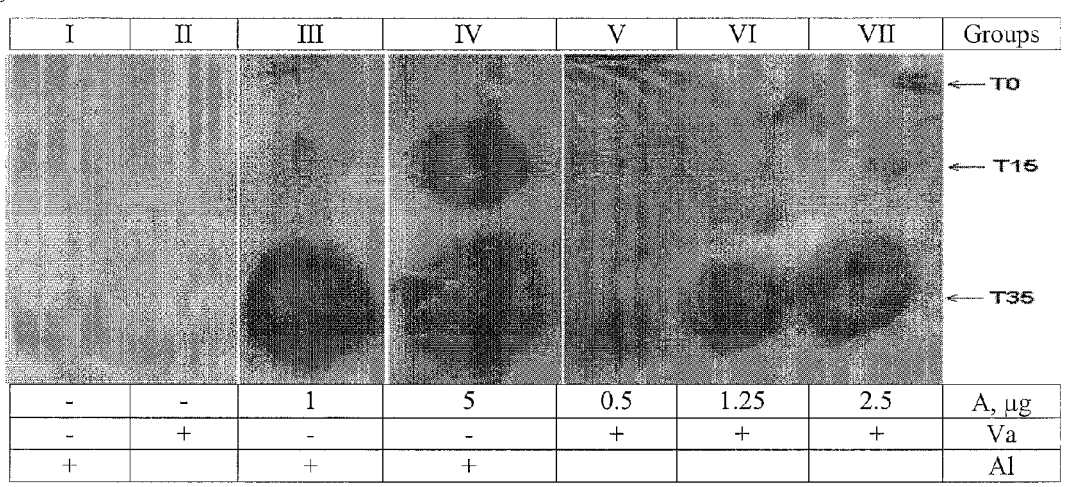
FIG. 10: It shows the reduction of the allergen-specific IgE by the vaccine composition (Group V to VII) as compared to positive controls (Groups III and IV), as measured by Passive Cutaneous Anaphylaxis. Sera were extracted at days 0 (To), at the time of the second dose (T15) and 14 days after the second dose (T35). The response in the groups (V-VII) is lower than in the groups immunized with alum-adsorbed allergen (III and IV). No response was observed in negative controls (I and II). Legend: "−" and "+", indicates the absence or presence of each vaccine ingredient, respectively FIG. 11. It is referred to the allergen-specific antibody response to allergen-proteoliposome conjugates. Mice were immunized with two doses of 5 µg of Der s 1, in different variants: A (free allergen); A-P (conjugated to Proteoliposome); [A-P]Al (Conjugate adsorbed into Aluminum Hydroxide). The response was evaluated at week 8 after the first immunization. The vertical bars indicate the standard deviation.
Figure 11:
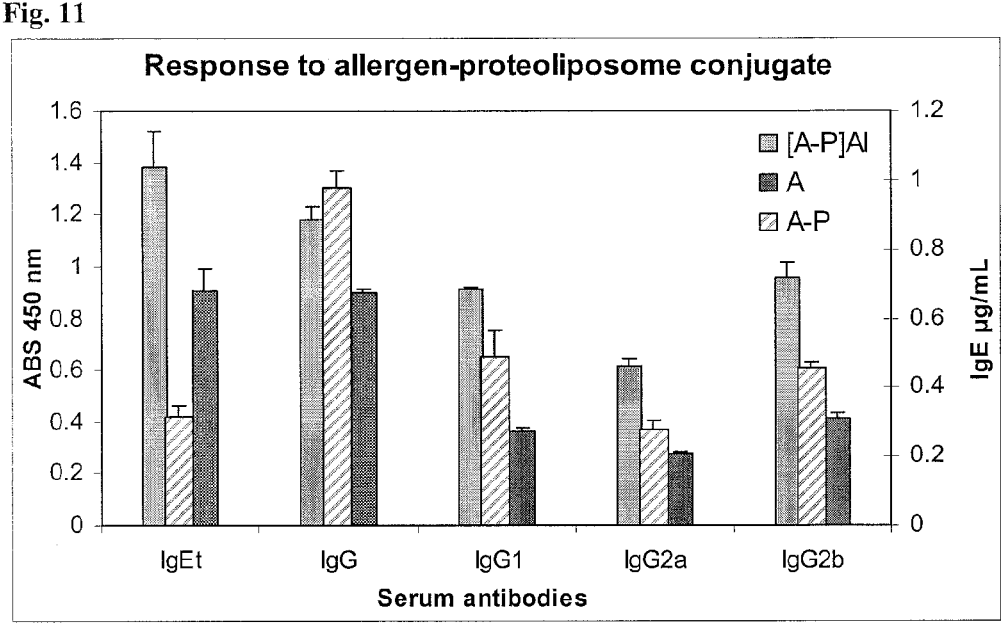

What is claimed is:
1. A vaccine composition for diminishing type I anaphylactic hypersensitivity to domestic mites and inducing a Th-1 type immune response to said mites comprising:
  a) a proteoliposome from the outer membrane of *Neisseria mentingitidis;*
  b. at least one allergen from domestic mites; and
  c) aluminum hydroxide as a depot adjuvant.

2. The vaccine composition of claim 1, wherein said composition contains between 20 and 75 µg of proteoliposome per dose.

3. The vaccine composition of claim 1, wherein said allergen is from domestic mites of the *Dermatophagoides* genus.

4. The vaccine composition of claim 3, wherein said allergen is from domestic mites of the *Dermatophagoides siboney* species.

5. The vaccine composition of claim 3, wherein the allergens are the Group 1 allergens selected from Der s 1, Der p 1 and Der f 1 allergens.

6. A method of treatment of type I anaphylactic hypersensitivity to domestic mites in a patient in need of such treatment, said method comprises administering the vaccine composition of claim 1 in 2 to 4 doses by parenteral or mucosal administration, with a time interval between said doses of 2 to 6 weeks.

7. The vaccine composition according to claim 1, wherein the allergen: proteoliposome mass ratio is from 0.1:10 to 1.0:10, and the allergen content is between 0.25 and 7.5 µg per administration dose.

8. The vaccine composition of claim 1, wherein the mass ratio of aluminum hydroxide depot adjuvant to proteoliposome is from 10:1 to 25:1 and the content of aluminum hydroxide is between 250 and 1000 µg per administration dose.

9. A method for treating type I anaphylactic hypersensitivity in a patient in need of said treatment, and said method comprises:
(a) preparing a composition comprising;
(i) proteoliposome from the outer membrane of *Neisseria meningitidis*, (ii) at least one allergen from domestic mites and (iii) aluminum hydroxide depot adjuvant; and
(b) administering the composition to the patient in 2 to 4 doses by a parenteral or mucosal route with a time interval between said doses of 2 to 6 weeks.

10. The method of claim 9, wherein said allergen is from domestic mites of the *Dermatophagoides siboney* species.

11. The method of claim 9, wherein the allergen: proteoliposome mass ratio is from 0.1:10 to 1:10, and the allergen content is between 0.25 and 7.5 µg per administration dose.

12. The method of claim 9, wherein the mass ratio of aluminum hydroxide adjuvant to proteoliposome is from 10:1 to 25:1 and the content of aluminum hydroxide is between 250 and 1000 µg per administration dose.

13. The method of claim 9, wherein the type I anaphylactic hypersensitivity is effectively treated within 6 to 24 weeks.

14. A method for producing a Th-1 type immune response to domestic mites in a patient, said method comprising:
(a) providing a proteoliposome from the meningococcal outer membrane of *Neisseria meningitidis;*
(b) providing a formulation comprising,
(i) said proteoliposome;
(ii) at least one allergen from domestic mites; and
(iii) aluminum hydroxide as a depot adjuvant; and
(c) administering said formulation in a patient by parenteral or mucosal administration;
whereby a Th-1 type immune response is induced in the patient.

15. The method of claim 14, wherein said allergen is from domestic mites of the *Dermatophagoides* genus.

16. The method of claim 14, wherein said allergen is from domestic mites of the *Dermatophagoides siboney* species.

17. The method of claim 14, said response further comprises an allergen-specific IgG.

* * * * *